United States Patent [19]
Sutliff et al.

[11] Patent Number: 6,066,781
[45] Date of Patent: May 23, 2000

[54] PRODUCTION OF MATURE PROTEINS IN PLANTS

[75] Inventors: Thomas D. Sutliff, Rocklin; Raymond L. Rodriguez, Davis, both of Calif.

[73] Assignee: Applied Phytologics, Inc., Sacramento, Calif.

[21] Appl. No.: 09/023,173

[22] Filed: Feb. 13, 1998

Related U.S. Application Data

[60] Provisional application No. 60/038,168, Feb. 13, 1997.

[51] Int. Cl.$^7$ .............................. C12N 15/82; C12N 5/04; C12N 15/29; A01H 4/00
[52] U.S. Cl. ........................ 800/278; 536/23.4; 536/23.6; 536/23.1; 536/24.1; 435/69.1; 435/468; 435/204; 435/70.1; 435/320.1; 800/278; 800/320.2; 800/284; 800/295
[58] Field of Search .................................. 536/23.4, 23.6, 536/23.1, 24.1; 435/69.1, 468, 204, 70.1, 320.1; 800/278, 320.2, 284, 295

[56] References Cited

U.S. PATENT DOCUMENTS

| | | | |
|---|---|---|---|
| 5,460,952 | 10/1995 | Yu et al. | 435/69.1 |
| 5,543,576 | 8/1996 | Van Ooijen et al. | 800/317.3 |
| 5,650,307 | 7/1997 | Sijmons et al. | 435/69.6 |
| 5,677,474 | 10/1997 | Rogers | 800/288 |
| 5,689,052 | 11/1997 | Brown et al. | 800/302 |
| 5,714,474 | 2/1998 | Van Ooijen et al. | 514/44 |
| 5,716,802 | 2/1998 | Sijmons et al. | 435/69.1 |

FOREIGN PATENT DOCUMENTS

| | | |
|---|---|---|
| 0 090 505 A2 | 5/1983 | European Pat. Off. . |
| 0 348 348 | 12/1989 | European Pat. Off. . |
| WO 90 01551 | 2/1990 | WIPO . |
| WO 91 02066 | 2/1991 | WIPO . |
| WO 92 01042 | 1/1992 | WIPO . |
| WO 95/14099 | 5/1995 | WIPO . |

OTHER PUBLICATIONS

Zhu et al. Nature, 1989, vol. 8:483–484.
Perlino et al., "The Human $\alpha^1$–Antitrypsin Gene is Transcribed from Two Different Promoters in Macrophages and Hepatocytes," *EMBO J.* 6:2767–2771 (1987).
Vasantha, N. et al., "Genes for Alkaline Protease and Neutral Protease from *Bacillus amyloliquefaciens* Contain a Large Open Reading Frame Between the Regions Coding for Signal Sequence and Mature Protein," *Journal of Bacteriology.* 159: (3) 811–819 (1984).
Chan, M–T., et al., "Novel gene expression system for plant cells based on induction of α–amylase promoter by carbohydrate starvation," J. of Biological Chemistry 269(69):17635–17641 (1994).
Jensen, L.G., et al., "Transgenic Barley expressing a protein–engineered, thermostable (1,3–1,4)–β–flucanase during germination," Proc. Natl. Acad. Sci. USA 93(8): 3487–3491 (1996).
Terashima, M., et al., "Production of functional human α–1–antitrypsin by rice cell culture; expression and protein secretion in callus culture (conference abstract)," Abstr. Pap. Am. Chem. Soc. Abstract #018, ACS National Meeting, Las Vegas, NV, Sep. 7–11 (1997).
Thomas, B.R., et al., "Gene Regulation and Protein Secretion from the Plant Cell Cultures: The Rice α–Amylase System," Advances in Plant Biotechnology pp. 37–55 (1994).
Napoli et al. The Plant Cell. 1989. vol. 2:278–289.
Chan et al. J. of Biological Chemistry. 1994. vol. 269: 17635–17641.
Mitsunaga et al. 1994. vol. 11: 1948–1953.
Huang et al. Nucleic Acid Research. 1990. vol. 18: 7007–7014.
Zhu et al. Nature. 1989. vol. 339: 483–484.

*Primary Examiner*—Elizabeth F. McElwain
*Assistant Examiner*—Ousama M-Faiz Zaghmout
*Attorney, Agent, or Firm*—Joanne R. Petithory; Peter J. Dehlinger

[57] ABSTRACT

A chimeric gene for use in producing a mature protein in secreted form by stably transformed plant cells is disclosed. The gene includes a DNA coding sequence encoding a fusion protein having an (i) N-terminal moiety corresponding to the portion of the rice α-amylase signal sequence peptide identified by SEQ ID: 1 and, (ii) immediately adjacent the C-terminal amino acid of said portion, a protein moiety corresponding to the protein to be produced. Also disclosed are a fusion protein encoded by the gene, and a method of producing a mature protein in secreted form by plant cells.

13 Claims, 3 Drawing Sheets

```
non-codon optimized  ATG AAG AAC ACC AGC AGC TTG TGT TTG CTG CTC CTC GTG GTG CTC TGC AGC TTG ACC TGT AAC TCG GGC CAG GCG
codon optimized      ATG AAG AAC ACC AGC TCC CTC CTG CTG CTG CTG GTC GTG CTC CTG CTG TCC TTG ACC TGC AAC AGC GGC CAG GCC
amino acid sequence  Met Lys Asn Thr Ser Ser Leu Cys Leu Leu Leu Val Val Leu Leu Cys Ser Leu Thr Cys Asn Ser Gly Gln Ala
```

PRODUCTION OF MATURE PROTEINS IN PLANTS

This application claims the priority of U.S. Provisional Application No. 60/038,168 filed Feb. 13, 1997, which is incorporated herein by reference.

FIELD OF THE INVENTION

The present invention relates to the production of mature proteins in plant cells, and in particular, to the production of proteins in mature secreted form.

BACKGROUND OF THE INVENTION

Many commercially important therapeutic proteins, including erythropoietin (EPO), tissue plasminogen activator (t-PA), urokinase and prourokinase, growth hormones, cytokines, factor VIII, epoetin-α, granulocyte colony stimulating factor, and vaccines, are produced by recombinant methods, typically by microbial fermentation. More recently, methods using mammalian cell culture or transgenic animals have been employed in producing some therapeutic proteins, and have the advantage of producing protein glycosylation that may confer advantages in terms of increased stability or activity of the proteins.

Once a protein has been approved for human therapeutic use, it is generally desirable, where alternative methods of synthesis are sought, to alter the synthesized protein as little as possible. Thus, for example, if the approved protein has a known sequence with given N- and C-terminal residues, it is desirable that any new method of protein synthesis be capable of producing a protein whose sequence is identical to that of the already approved mature protein.

SUMMARY OF THE INVENTION

In one aspect, the invention includes a chimeric gene for use in producing, in a transgenic monocot plant or in a culture of plant cells transformed with the chimeric gene, a mature protein other than a plant α-amylase. The gene includes a DNA coding sequence encoding a fusion protein having an (i) N-terminal moiety corresponding to the portion of the rice α-amylase signal sequence peptide identified by SEQ ID NO: 1 and, and (ii) immediately adjacent the C-terminal amino acid of this signal-sequence portion, a protein moiety corresponding to the mature protein to be produced.

The gene may include, upstream of the DNA coding sequence, a monocot promoter which is inducible by addition or depletion of a small molecule. The promoter may be derived, for example, from the RAmy1A, RAmy1B, RAmy2A, RAmy3A, RAmy3B, RAmy3C, RAmy3D, or RAmy3E rice α-amylase genes, or from the pM/C, gKAmy141, gKAmy155, Amy32b, or HV18 barley α-amylase genes. Where the gene is employed in protein production in a monocot cell culture, preferred promoters are the RAmy3D and RAmy3E gene promoters, which are upregulated by sugar depletion in cell culture. Where the gene is employed in protein production in germinating seeds, a preferred promoter is the RAmy1A gene promoter, which is upregulated by gibberellic acid during seed germination.

The gene may further include, between the promoter and coding sequences, the 5' untranslated region (5' UTR) of an inducible monocot gene, such as the 5' UTR derived from one of the rice or barley α-amylase genes mentioned above. One preferred 5' UTR is that from the RAmy1A gene, which is effective to enhance the stability of the gene transcript. The gene may further include, downstream of the coding sequence, the 3' untranslated region (3' UTR) from an inducible monocot gene, such as one of the rice or barley α-amylase genes mentioned above. One preferred 3' UTR is from the RAmy1A gene.

The coding sequence for the signal sequence peptide identified by SEQ ID NO: 1 may have the native sequence identified by SEQ ID NO: 2, or may have a codon-optimized sequence, such as represented by SEQ ID NO: 3.

Also disclosed is a fusion protein having an N-terminal region corresponding to the portion of the rice α-amylase signal sequence peptide identified by SEQ ID NO: 1 and, immediately adjacent the C-terminal amino acid of this signal-sequence portion, a heterologous protein other than a monocot α-amylase gene. This fusion protein, when produced in monocot plant cell culture or in plant tissue, is secreted by the cells and cleaved at the N-terminal amino acid of the heterologous protein, yielding a mature protein with the correct N-terminal sequence.

In another aspect, the invention includes a method of producing, in a monocot plant tissue or plant cell culture, a mature heterologous protein, other than a monocot α-amylase gene, having a known N-terminal amino acid sequence. The method includes (a) obtaining monocot cells transformed with a chimeric gene of the type described above, (b) cultivating the transformed cells under conditions effective to induce the gene's regulatory region, thereby to promote expression of the fusion protein and secretion of the mature protein; and (c) isolating mature heterologous protein secreted by the cells.

These and other objects and features of the invention will be more fully understood when the following detailed description of the invention is read in conjunction with the accompanying drawings.

BRIEF DESCRIPTION OF THE FIGURES

FIG. 1 shows, in the lower row, the amino acid sequence of a RAmy3D signal sequence portion employed in the invention, identified as SEQ ID NO: 1; in the middle row, the corresponding native coding sequence, identified as SEQ ID NO: 2; and in the upper row, a corresponding codon-optimized sequence, identified as SEQ ID NO: 3;

FIG. 3 shows an N-terminal sequence for mature $\alpha_1$-antitrypsin (AAT) produced in accordance with the invention, identified herein as SEQ ID NO: 9.

BRIEF DESCRIPTION OF THE SEQUENCES

Figure 2:
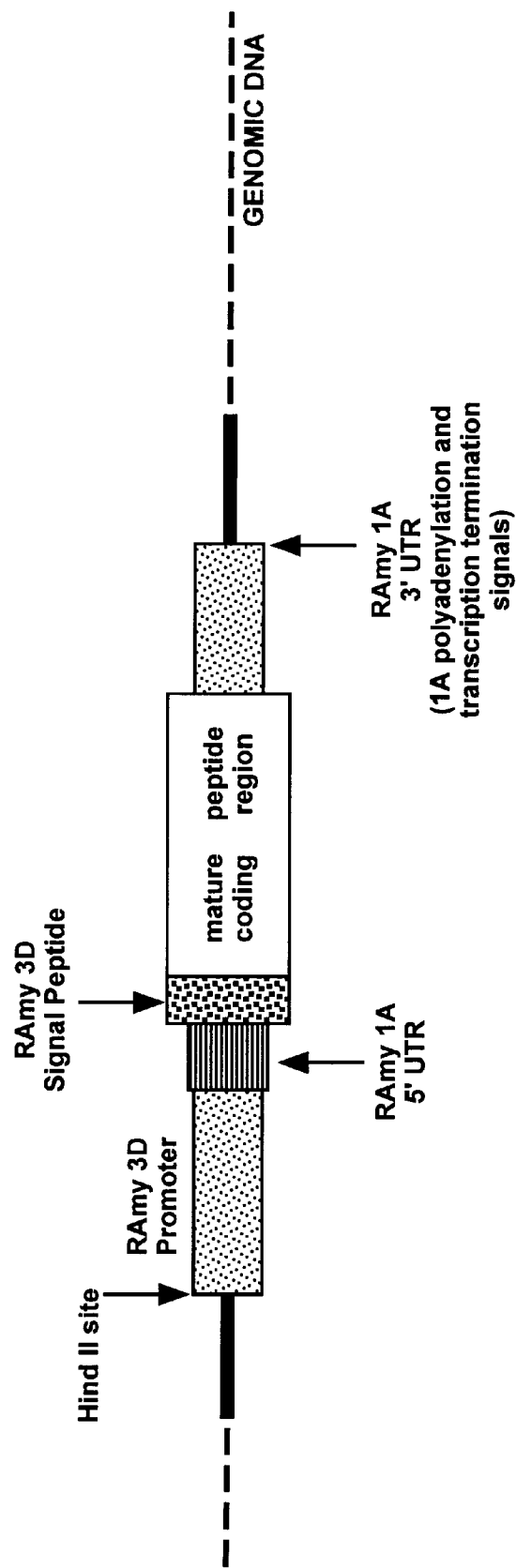
FIG. 2 illustrates the components of a chimeric gene constructed in accordance with an embodiment of the invention.

SEQ ID NO: 1 is the amino acid sequence of the RAmy3D signal peptide;

SEQ ID NO: 2 is the native sequence encoding the RAmy3D signal peptide;

SEQ ID NO: 3 is a codon-optimized sequence encoding the RAmy3D signal peptide;

SEQ ID NO: 4 is a codon-optimized coding sequence of the RAmy3D signal peptide-prosubtilisin BPN' fusion protein;

SEQ ID NO: 5 is a codon-optimized coding sequence of the RAmy3D signal peptide-mature $\alpha_1$-antitrypsin fusion protein;

SEQ ID NO: 6 is a coding sequence of the RAmy3D signal peptide-mature antithrombin III fusion protein, in which a codon-optimized RAmy3D coding sequence is fused to native ATIII coding sequence;

SEQ ID NO: 7 is the 5' UTR derived from the RAmy1A gene;

SEQ ID NO: 8 is the 3' UTR derived from the RAmy1A gene; and

SEQ ID NO: 9 is the N-terminal sequence of mature $\alpha_1$-antitrypsin produced in accordance with the invention.

SEQ ID NO: 10 is a codon-optimized sequence encoding the 3D signal peptide-mature AAT fusion protein with flanking NotI/XhoI sites as described in Example 1G.

SEQ ID NO: 11 is an oligonucleotide used to prepare the intermediate p3DProSig construct of Example 1;

SEQ ID NO: 12 is the complement of SEQ ID NO: 11;

SEQ ID NO: 13 is an oligonucleotide used to prepare the intermediate p3DProSigENDlink construct of Example 1;

SEQ ID NO: 14 is the complement of SEQ ID NO: 13;

SEQ ID NO: 15 is one of six oligonucleotides used to prepare the intermediate p1AProSig construct of Example 1;

SEQ ID NO: 16 is one of six oligonucleotides used to prepare the intermediate p1AProSig construct of Example 1;

SEQ ID NO: 17 is one of six oligonucleotides used to prepare the intermediate p1AProSig construct of Example 1;

SEQ ID NO: 18 is one of six oligonucleotides used to prepare the intermediate p1AProSig construct of Example 1;

SEQ ID NO: 19 is one of six oligonucleotides used to prepare the intermediate p1AProSig construct of Example 1;

SEQ ID NO: 20 is one of six oligonucleotides used to prepare the intermediate p1AProSig construct of Example 1;

SEQ ID NO: 21 is the mutagenic oligonucleotide used to introduce a NotI site into p3Dv2.0 according to Example 1;

SEQ ID NO: 22 is an oligonucleotide used to prepare the p3D-AAT2.1.1 expression vector according to Example 1; and SEQ ID NO: 23 is an oligonucleotide used to prepare the p3D-AAT2.1.1 expression vector according to Example 1.

DETAILED DESCRIPTION OF THE INVENTION

I. Definitions

The terms below have the following meaning, unless indicated otherwise in the specification.

"Cell culture" refers to cells and cell clusters, typically callus cells, growing on or suspended in a suitable growth medium.

"Germination" refers to the breaking of dormancy in a seed and the resumption of metabolic activity in the seed, including the production of enzymes effective to break down starches in the seed endosperm.

"Inducible" means a promoter that is upregulated by the presence or absence of a small molecules. It includes both indirect and direct inducement.

"Inducible during germination" refers to promoters which are substantially silent but not totally silent prior to germination but are turned on substantially (greater than 25%) during germination and development in the seed. Examples of promoters that are inducible during germination are presented below.

"Small molecules", in the context of promoter induction, are typically small organic or bioorganic molecules less than about 1 kilodalton. Examples of such small molecules include sugars, sugar-derivatives (including phosphate derivatives), and plant hormones (such as, gibberellic or abscisie acid).

"Specifically regulatable" refers to the ability of a small molecule to preferentially affect transcription from one promoter or group of promoters (e.g., the $\alpha$-amylase gene family), as opposed to non-specific effects, such as, enhancement or reduction of global transcription within a cell by a small molecule.

"Heterologous DNA" or "foreign DNA" refers to DNA which has been introduced into plant cells from another source, or which is from a plant source, including the same plant source, but which is under the control of a promoter or terminator that does not normally regulate expression of the heterologous DNA.

"Heterologous protein" is a protein, including a polypeptide, encoded by a heterologous DNA.

A "transcription regulatory region" or "promoter" refers to nucleic acid sequences that influence and/or promote initiation of transcription. Promoters are typically considered to include regulatory regions, such as enhancer or inducer elements.

"Operably linked" refers to components of a chimeric gene or an expression cassette that function as a unit to express a heterologous protein. For example, a promoter operably linked to a heterologous DNA, which encodes a protein, promotes the production of functional mRNA corresponding to the heterologous DNA.

A "product" encoded by a DNA molecule includes, for example, RNA molecules and polypeptides.

"Removal" in the context of a metabolite includes both physical removal as by washing and the depletion of the metabolite through the absorption and metabolizing of the metabolite by the cells.

"Substantially isolated" is used in several contexts and typically refers to the at least partial purification of a protein or polypeptide away from unrelated or contaminating components. Methods and procedures for the isolation or purification of proteins or polypeptides are known in the art.

"Stably transformed" as used herein refers to a cereal cell or plant that has foreign nucleic acid stably integrated into its genome which is transmitted through multiple generations.

"Codon optimization" refers to changes in the coding sequence of a gene to replace native codons with those corresponding to optimal codons in the host plant.

"Chimeric gene" refers to a gene construct containing a DNA coding sequence encoding a fusion protein having an (i) N-terminal moiety corresponding to the portion of the rice $\alpha$-amylase signal sequence peptide identified by SEQ ID NO: 1 and, (ii) immediately adjacent the C-terminal amino acid of this signal-sequence portion, a protein moiety corresponding to a mature heterologous protein.

A DNA sequence is "derived from" a gene, such as a rice or barley $\alpha$-amylase gene, if it corresponds in sequence to a segment or region of that gene. Segments of genes which may be derived from a gene include the promoter region, the 5' untranslated region, and the 3' untranslated region of the gene.

II. Chimeric Gene

In one aspect, the invention includes a DNA coding sequence encoding a fusion protein having an (i) N-terminal moiety corresponding to the portion of the rice $\alpha$-amylase signal sequence peptide identified by SEQ ID NO: 1 and, (ii) immediately adjacent the C-terminal amino acid of this signal-sequence portion, a protein moiety corresponding to the mature protein to be produced.

The amino acid sequence of the signal sequence, i.e., SEQ ID NO: 1, is shown at the bottom in FIG. 1. The native coding sequence for this peptide, derived from the rice α-amylase RAmy3D gene, is shown in the middle row in FIG. 1, and is identified herein as SEQ ID NO: 2. In another embodiment of the invention, the coding sequence in the chimeric gene, in at least the coding region for the signal sequence, may be codon-optimized for optimal expression in plant cells, e.g., rice cells. The upper row in FIG. 1 shows one codon-optimized coding sequence for the RAmy3D signal sequence, identified herein as SEQ ID NO: 3.

In the method for codon optimization applied above, the coding sequences from rice were analyzed for codon frequency for each amino acid, and the most frequent codon was selected for each amino acid. The optimal codons selected in this manner for rice are shown in Table 1.

TABLE 1

| Amino Acid | Rice Preferred Codon | Barley Preferred Codon |
|---|---|---|
| Ala A | GCC | |
| Arg R | CGC | |
| Asn N | AAC | |
| Asp D | GAC | |
| Cys C | UGC | |
| Gln Q | CAG | |
| Glu E | GAG | |
| Gly G | GGC | |
| His H | CAC | |
| Ile I | AUC | |
| Leu L | CUC | |
| Lys K | AAG | |
| Phe F | UUC | |
| Pro P | CCG | CCC |
| Ser S | AGC | UCC |
| Thr T | ACC | |
| Tyr Y | UAC | |
| Val V | GUC | GUG |
| stop | UAA | UGA |

Typical mature proteins which are encoded by the chimeric gene include commercially important therapeutic proteins and polypeptides, including erythropoietin (EPO), tissue plasminogen activator (t-PA), urokinase and prourokinase, growth hormones, cytokines, factor VIII, epoetin-α, granulocyte colony stimulating factor, and vaccines. The coding sequence for the mature forms of these proteins are available from a variety of reference and sequence database sources. As indicated above, the coding sequence in the chimeric gene is constructed such that the final "Ala" codon in the signal sequence is immediately followed by the codon for the N-terminal amino acid in the mature form of the mature heterologous protein. Several exemplary chimeric genes, in accordance with the present invention, are identified herein as follows:

SEQ ID NO: 4, corresponding to codon-optimized coding sequences of the fusion protein RAmy3D signal sequence/ prosubtilisin BPN'. In this instance, prosubtilisin is considered the "mature" protein, in that secreted prosubtilisin can autocatalyze to active, mature subtilisin.

SEQ ID NO: 5, corresponding to codon-optimized coding sequences of the fusion protein RAmy3D signal sequence/ mature $\alpha_1$-antitrypsin; and SEQ ID NO: 6, corresponding to the codon-optimized coding sequences of the RAmy3D signal sequence in the fusion protein and the native coding sequence of mature antithrombin III.

The chimeric gene also preferably includes, upstream of the DNA coding sequence, a monocot promoter which is inducible by addition or depletion of a small molecule. Representative promoters include the promoters from the rice α-amylase RAmy1A, RAmy1B, RAmy2A, RAmy3A, RAmy3B, RAmy3C, RAmy3D, and RAmy3E genes, and from the pM/C, gKAmy141, gKAmy155, Amy32b, and HV18 barley α-amylase genes. These promoters are described, for example, in *ADVANCES IN PLANT BIOTECHNOLOGY*, Ryu, et al, Eds., Elsevier, Amsterdam, 1994, p.37, and references cited therein.

Where the gene is employed in protein production in a monocot cell culture, preferred promoters are the RAmy3E and RAmy3D gene promoters, which are upregulated by sugar depletion in cell culture. Where the gene is employed in protein production in germinating seeds, a preferred promoter is the RAmy1A gene promoter, which is upregulated by gibberellic acid during seed germination.

The gene may further include, between the promoter and coding sequences, the 5' untranslated region (5' UTR) of an inducible monocot gene, such as the 5' UTR derived from one of the rice or barley α-amylase genes mentioned above. One preferred 5' UTR is that derived from the RAmy1A gene, which is effective to enhance the stability of the gene transcript. This 5' UTR has the sequence given by SEQ ID NO: 7 herein.

The gene may also include, downstream of the coding sequence, the 3' untranslated region (3' UTR) from an inducible monocot gene, such as one of the rice or barley α-amylase genes mentioned above. One preferred 3' UTR is that derived from the RAmy1A gene, whose sequence is given by SEQ ID NO: 8. This sequence includes non-coding sequence 5' to the polyadenylation site, the polyadenylation site and the transcription termination sequence. The transcriptional termination region may be selected, particularly for stability of the mRNA to enhance expression. Polyadenylation tails, Alber and Kawasaki, *Mol. and Appl. Genet.* 1:419–434 (1982) are also commonly added to the expression cassette to optimize high levels of transcription and proper transcription termination, respectively. Polyadenylation sequences include but are not limited to the Agrobacterium octopine synthetase signal, Gielen, et al., *EMBO J.* 3:835–846 (1984) or the nopaline synthase of the same species Depicker, et al., *Mol. Appl. Genet.* 1:561–573 (1982).

FIG. 2 shows the elements of one preferred chimeric gene constructed in accordance with the invention, and intended particularly for use in protein expression in a rice cell suspension culture. The gene includes, in a 5' to 3' direction, the promoter from the RAmy3D gene, which is inducible in cell culture with sugar depletion, the 5' UTR from the RAmy1A gene, which confers enhanced stability on the gene transcript, the RAmy3D signal sequence coding region, as identified above, the coding region of a heterologous protein to be produced, and a 3' UTR region from the RAmy1A gene.

III. Plant Transformation

For transformation of plants, the chimeric gene of the invention is placed in a suitable expression vector designed for operation in plants. The vector includes suitable elements of plasmid or viral origin that provide necessary characteristics to the vector to permit the vectors to move DNA from bacteria to the desired plant host. Suitable transformation vectors are described in related application PCT WO 95/14099, published May 25, 1995, which is incorporated by reference herein. Suitable components of the expression vector, including the chimeric gene described in Section II, are discussed below. One exemplary vector is the p3Dv1.0 vector described in Example 1 below.

A. Transformation Vector

Vectors containing a chimeric gene of the present invention may also include selectable markers for use in plant cells (such as the nptII kanamycin resistance gene, for selection in kanamycin-containing or the phosphinothricin acetyltransferase gene, for selection in medium containing phosphinothricin (PPT).

The vectors may also include sequences that allow their selection and propagation in a secondary host, such as sequences containing an origin of replication and a selectable marker such as antibiotic or herbicide resistance genes, e.g., HPH (Hagio et al., *Plant Cell Reports* 14:329 (1995) and van der Elzer, *Plant Mol. Biol.* 5:299–302 (1985). Typical secondary hosts include bacteria and yeast. In one embodiment, the secondary host is *Escherichia coli*, the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens*.

The vector described in Example 1, and having a promoter from the RAmy3D gene, is suitable for use in a method of mature protein production in cell culture, where the RAmy3D promoter is induced by sugar depletion in cell culture medium. Other promoters may be selected for other applications, as indicated above. For example, for mature protein expression in germinating seeds, the coding sequence may be placed under the control of the rice α-amylase RAmy1A promoter, which is inducible by gibberellic acid during seed germination.

B. Transformation of Plant Cells

The plants used in the process of the present invention are derived from monocots, particularly the members of the taxonomic family known as the Gramineae. This family includes all members of the grass family of which the edible varieties are known as cereals. The cereals include a wide variety of species such as wheat (Triticum sps.), rice (Oryza sps.) barley (Hordeum sps.) oats, (Avena sps.) rye (Secale sps.), corn (Zea sps.) and millet (Pennisettum sps.). In the present invention, preferred family members are rice and barley.

Plant cells or tissues derived from the members of the family are transformed with expression constructs (i.e., plasmid DNA into which the chimeric gene of the invention has been inserted) using a variety of standard techniques (e.g., electroporation, protoplast fusion or microparticle bombardment). In the present invention, particle bombardment is the preferred transformation procedure.

Various methods for direct or vectored transformation of plant cells, e.g., plant protoplast cells, have been described, e.g., in above-cited PCT application WO 95/14099. As noted in that reference, promoters directing expression of selectable markers used for plant transformation (e.g., nptII) should operate effectively in plant hosts. One such promoter is the nos promoter from native Ti plasmids, Herrera-Estrella, et al., *Nature* 303:209–213 (1983). Others include the 35S and 19S promoters of cauliflower mosaic virus, Odell, et al., *Nature* 313:810–812 (1985), and the 2' promoter, Velten, et al., *EMBO J.* 3:2723–2730 (1984).

In one preferred embodiment, the embryo and endosperm of mature seeds are removed to exposed scutellum tissue cells. The cells may be transformed by DNA bombardment or injection, or by vectored transformation, e.g., by Agrobacterium infection after bombarding the scuteller cells with microparticles to make them susceptible to Agrobacterium infection (Bidney et al., *Plant Mol. Biol.* 18:301–313 (1992)).

One preferred transformation follows the methods detailed generally in Sivamani, E. et al., *Plant Cell Reports* 15:465 (1996); Zhang, S., et al., *Plant Cell Reports* 15:465 (1996); and Li, L., et al., *Plant Cell Reports* 12:250 (1993).

IV. Cell Culture Production of Mature Protein

Transgenic cells, typically callus cells, are cultured under conditions that favor plant cell growth, until the cells reach a desired cell density, then under conditions that favor expression of the mature protein under the control of the given promoter. Preferred cell culture conditions are disclosed in Example 2. Purification of the mature protein secreted into the medium is by standard techniques known by those of skill in the art.

Figure 3:
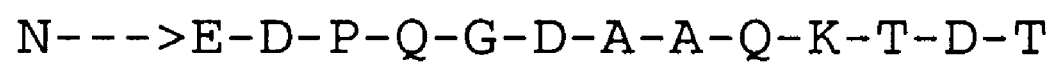

To demonstrate that the mature protein is produced in secreted form, with the desired N-terminus, a chimeric gene constructed as above, and having the coding sequence for mature $\alpha_1$-antitrypsin was expressed and secreted in cell culture as described in Example 2. The isolated protein then sequenced at its N-terminal region, yielding the N-terminal sequence shown in FIG. 3. This sequence, which is identified herein as SEQ ID NO: 9, has the same N-terminal residue as native mature $\alpha_1$-antitrypsin

V. Production of Mature Protein in Germinating Seeds

In this embodiment, monocot cells transformed as above are used to regenerate plants, seeds from the plants are harvested and then germinated, and the mature protein is isolated from the germinated seeds.

Plant regeneration from cultured protoplasts or callus tissue is carried by standard methods, e.g., as described in Evans et al., *HANDBOOK OF PLANT CELL CULTURES* Vol. 1: (MacMillan Publishing Co. New York, 1983); and Vasil I. R. (ed.), *CELL CULTURE AND SOMATIC CELL GENETICS OF PLANTS*, Acad. Press, Orlando, Vol. I, 1984, and Vol. III, 1986, and as described in the above-cited PCT application.

The transgenic seeds obtained from the regenerated plants are harvested, and prepared for germination by an initial stepping step, followed by malting in the presence of gibberellic acid, as detailed, for example, in above-identified PCT application WO 95/14099.

The mature protein secreted from aleurone cells into the endosperm tissue of the seed can be isolated by standard methods. Typically, the seeds are mashed to disrupt tissues, the seed mash is suspended in a protein extraction buffer, and the protein is isolated from the buffer by conventional means.

VI. Fusion Protein

In another aspect, the present invention relates to a fusion protein having an N-terminal region corresponding to the portion of the rice α-amylase signal sequence peptide identified by SEQ ID NO: 1 and, immediately adjacent to the C-terminal amino acid of said portion, a heterologous protein other than a monocot α-amylase gene.

The fusion protein may include, in addition to the signal sequence identified by SEQ ID NO: 1, any heterologous protein, e.g., a protein other than a plant α-amylase, and is preferably a commercial therapeutic protein of peptide such as erythropoietin (EPO), tissue plasminogen activator (t-PA), urokinase and prourokinase, growth hormones, cytokines, factor VIII, epoetin-α, granulocyte colony stimulating factor, and vaccines.

The following examples are provided by way of illustration only and not by way of limitation. Those of skill will readily recognize a variety of noncritical parameters which could be changed or modified to yield essentially similar results.

General Methods

Generally, the nomenclature and laboratory procedures with respect to standard recombinant DNA technology can be found in Sambrook, et al., *MOLECULAR CLONING—A LABORATORY MANUAL,* Cold Spring Harbor Laboratory, Cold Spring Harbor, N.Y. (1989), and in Gelvin and Schilperoot, *PLANT MOLECULAR BIOLOGY* (1988). Other general references are provided throughout this document. The procedures therein are known in the art and are provided for the convenience of the reader.

EXAMPLE 1

Construction of a Transforming Vector Containing a Codon-Optimized $\alpha_1$-antitrypsin Sequence A. Hgromycin Resistance Gene Insertion The 3 kb BamHI fragment containing the 35S promoter-Hph-NOS was removed from the plasmid pMON410 (Monsanto, St. Louis, Mo.) and placed into an site-directed mutagenized Bg/II site in the pUC18 at 1463 to form the plasmid pUCH18+.

B. Terminator Insertion pOSg1ABK5 is a 5 kb BamHI-KpnI fragment from lambda clone λOSg1A (Huang, et al., *Nuc. Acids Res.* 18:7007 (1990)) cloned into pBluescript KS- (Stratagene, San Diego, Calif.). Plasmid pOSg1ABK5 was digested with MspI and blunted with T4 DNA polymerase followed by SpeI digestion. The 350 bp terminator fragment was subcloned into pUC19 (New England BioLabs, Beverly, Mass.), which had been digested with BamHI, blunted with T4 DNA polymerase and digested with XbaI, to form pUC19/terminator.

C. RAmy3D Promoter Insertion

A 1.1 kb NheI-PstI fragment derived from p1AS1.5 (Huang, et al., *Plant Mol. Biol.* 23:737–747 (1993)), was cloned into the vector pGEM5zf- [multiple cloning site (MCS) (Promega, Madison, Wis.): ApaI, AatII, SphI, NcoI, SstII, EcoRV, SpeI, NotI, PstI, SalI, NdeI, SacI, MluI, NsiI] at the SpeI and PstI sites to form pGEM5zf-(3D/NheI-PstI). pGEM5zf-(3D/NheI-PstI) was then digested with PstI and SacI, and two non-kinased 30mers having the complementary sequences 5' GCTTG ACCTG TAACT CGGGC CAGGC GAGCT 3' (SEQ ID NO: 11) and 5' CGCCT AGCCC GAGTT ACAGG TCAAG CAGCT 3' (SEQ ID NO: 12) were ligated in to form p3DProSig. The promoter fragment prepared by digesting p3DProSig with NcoI, blunting with T4 DNA polymerase, and digesting with SstI was subcloned into pUC19/terminator which had been digested with EcoRI, blunted with T4 DNA polymerase and digested with SstI, to form p3DProSigEND.

D. Multiple Cloning Site Insertion p3DProSigEND was digested with SstI and SmaI followed by the ligation of a new synthetic linker fragment constructed with the non-kinased complementary oligonucleotides 5' AGCTC CATGG CCGTG GCTCG AGTCT AGACG CGTCC CC 3' (SEQ ID NO: 13) and 5' GGGGA CGCGT CTAGA CTCGA GCCAC GGCCA TGG 3' (SEQ ID NO: 14) to form p3DProSigENDlink.

E. p3DProSigENDlink Flanking Site Modification p3DProSigENDlink was digested with SalI and blunted with T4 DNA polymerase followed by EcoRV digestion. The blunt fragment was then inserted into pBluescript KS+ (Stratagene) in the EcoRV site so that the HindIII site is proximal to the promoter and the EcoRI is proximal to the terminator sequence. The HindIII-EcoRI fragment was then moved into the polylinker of pUCH18+ to form the p3Dv1.0 expression vector.

F. RAmy1A Promoter Insertion

A 1.9 kb NheI-PstI fragment derived from subclone pOSG2CA2.3 from lambda clone λOSg2 (Huang, et al., *Plant Mol. Biol.* 14:655–668 (1990)), was cloned into the vector pGEM5zf- at the SpeI and PstI sites to form pGEM5zf-(1A/NheI-PstI). pGEM5zf-(1A/NheI-PstI) was digested with PstI and SacI and two non-kinased 35mers and four kinased 32mers were ligated in, with the complementary sequences as follows: 5' GCATG CAGGT GCTGA ACACC ATGGT GAACA AACAC 3' (SEQ ID NO: 15); 5' TTCTT GTCCC TTTCG GTCCT CATCG TCCTC CT 3' (SEQ ID NO: 16); 5' TGGCC TCTCC TCCAA CTTGA CAGCC GGGAG CT 3' (SEQ ID NO: 17); 5' TTCAC CATGG TGTTC AGCAC CTGCA TGCTG CA 3' (SEQ ID NO: 18); 5' CGATG AGGAC CGAAA GGGAC AAGAA GTGTT TG 3' (SEQ ID NO: 19); 5' CCCGG CTGTC AAGTT GGAGG AGAGG CCAAG GAGGA 3' (SEQ ID NO: 20) to form p1AProSig. The HindIII-SacI 0.8 kb promoter fragment was subcloned from p1AProSig into the p3Dv1.0 vector digested with HindIII-SacI to yield the p1Av1.0 expression vector.

G. Construction of p3D-AAT Codon-Optimized Plasmid

The p3DV1.0 vector described above was modified as follows. The HindIII-EcoRI expression cassette fragment from p3Dv1.0 was moved into a NarI-lacking (Klenow filled) version of pUC19, creating p3Dv2.0. The HindIII-XbaI promoter fragment was cloned into pBluscript KS+ and a NotI site was introduced by means of a mutagenic oligonucleotide with the sequence 5' CCGTG TTCGA TAGTG AGCGG CCGCT AACCA CTACT GATC 3'(SEQ ID NO: 21). This mutagenized fragment was then placed back into p3Dv2.0 resulting in p3Dv2.0 (NotI). A synthesized, codon-optimized RAmy3D signal peptide-mature AAT NotI/XhoI fragment (SEQ ID NO: 10) was then cloned into the NotI/XhoI sites of p3Dv2.0 (NotI) forming p3D-AAT2.0. The NotI site was then used to insert the first exon (partial)-intron 1-second exon (partial) generated by PCR from pOSg1ABK5 with the NotI containing primers 5' GTTTC AGCTT ACACA GATGC GGCCG CCACC AGCAG CTTGT GT 3' (SEQ ID NO: 22) and 5' CCTTT CAACA TGTTG TAGCG GCCGC CCTGC TGCTT CCACG 3' (SEQ ID NO: 23) to create p3D-AAT2.1.1.

EXAMPLE 2

Production of Mature α-antitrypsin in Cell Culture

After selection of transgenic callus, callus cells were suspended in liquid culture containing AA2 media (Thompson, et al., *Plant Science* 47:123 (1986), at 3% sucrose, pH 5.8. Thereafter, the cells were shifted to phosphate-buffered media (20 mM phosphate buffer, pH 6.8) using 10 mL multi-well tissue culture plates and shaken at 120 rpm in the dark for 48 hours. The supernatant was then removed and stored at −80° C. prior to western blot analysis.

Supernatants were concentrated using Centricon-10 filters (Amicon Cat. #4207) and washed with induction media to remove substances interfering with electrophoretic migration. Samples were concentrated approximately 10 fold, and mature AAT was purified by SDS PAGE electrophoresis. The purified protein was extracted from the electrophoresis medium, and sequenced at its N-terminus, giving the sequence shown in FIG. 3, identified herein as SEQ ID NO: 9.

Although the invention has been described with reference to particular embodiments, it will be appreciated that a variety of changes and modifications can be made without departing from the invention.

What is claimed is:

1. A chimeric gene for use in producing, in monocot plant cells transformed with the chimeric gene, a mature protein other than a monocot α-amylase, comprising
   a DNA coding sequence encoding a fusion protein consisting of an N-terminal segment which is the rice α-amylase signal sequence identified by SEQ ID NO: 1 directly joined at its C-terminal amino acid to the N-terminal amino acid of a C-terminal segment which is the mature protein to be produced.

2. The chimeric gene of claim 1, which further comprises, upstream of said DNA coding sequence, a promoter from a rice RAmy3D gene.

3. The chimeric gene of claim 2, which further comprises, between said promoter and coding sequence, the 5' untranslated region from a rice RAmy1A gene.

4. The chimeric gene of claim 3, which further comprises, downstream of the coding sequence, the 3' untranslated region from a rice RAmy1A gene.

5. The chimeric gene of claim 3, wherein the 5' untranslated region has the sequence identified by SEQ ID NO: 7.

6. The chimeric gene of claim 1, wherein the coding sequence for the signal sequence peptide identified by SEQ ID NO: 1 has the nucleotide sequence identified by SEQ ID NO: 2.

7. The chimeric gene of claim 1, wherein the coding sequence for the signal sequence peptide identified by SEQ ID NO: 1 has the sequence identified by SEQ ID NO: 3.

8. The chimeric gene of claim 1, wherein the protein to be produced is pro-subtilisin BPN' (proBPN'), and the chimeric gene has the coding sequence identified by SEQ ID NO: 4.

9. A method of producing, in monocot plant cells, a mature heterologous protein, other than a monocot α-amylase, comprising
- (a) obtaining monocot plant cells transformed with a chimeric gene having (i) a RAmy3D rice promoter and (ii) a DNA coding sequence encoding a fusion protein consisting of an N-terminal segment which is the rice α-amylase signal sequence identified by SEQ ID NO: 1 directly joined to the mature heterologous protein, where said coding sequence is operably linked to said promoter,
- (b) cultivating the transformed monocot cells under conditions which promote production of the fusion protein and secretion of the mature protein; and
- (c) isolating the mature protein secreted from said cells, wherein the N-terminal amino acid of said mature protein secreted from said cells is the same as the N-terminal amino acid of said C-terminal segment.

10. The method of claim 9, wherein the chimeric gene further comprises, between said promoter and coding sequence, the 5' untranslated region from a rice RAmy1A gene.

11. The method of claim 10, wherein the chimeric gene further comprises, downstream of the coding region, the 3' untranslated region from a rice RAmy1A gene.

12. The method of claim 9, wherein the coding sequence for the signal sequence peptide identified by SEQ ID NO: 1 has the sequence identified by SEQ ID NO: 2.

13. The method of claim 9, wherein the coding sequence for the signal sequence peptide identified by SEQ ID NO: 1 has the sequence identified by SEQ ID NO: 3.

* * * * *

UNITED STATES PATENT AND TRADEMARK OFFICE
Certificate

Patent No. 6,066,781                                          Patented: May 23, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Thomas D. Sutliff, Rocklin, CA; Raymond L. Rodriguez, Davis, CA; and John M. Chandler, Davis, CA.

Signed and Sealed this Thirteenth Day of April 2004.

*AMY J. NELSON*
*Supervisory Patent Examiner*
Art Unit 1638

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 25 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (B) CLONE: RAmy3D signal peptide (xi) SEQUENCE DESCRIPTION: SEQ ID NO:1:

```
Met Lys Asn Thr Ser Ser Leu Cys Leu Leu Leu Leu Val Val Leu Cys
 1               5                  10                  15

Ser Leu Thr Cys Asn Ser Gly Gln Ala
            20                  25
```

(2) INFORMATION FOR SEQ ID NO:2:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (vii) IMMEDIATE SOURCE:
      (B) CLONE: RAmy3D signal peptide native coding sequence (xi) SEQUENCE DESCRIPTION: SEQ ID NO:2:

```
ATGAAGAACA CCAGCAGCTT GTGTTTGCTG CTCCTCGTGG TGCTCTGCAG CTTGACCTGT     60

AACTCGGGCC AGGCG                                                     75
```

(2) INFORMATION FOR SEQ ID NO:3:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (vii) IMMEDIATE SOURCE:
      (B) CLONE: RAmy3D signal codon-optimized coding sequence (xi) SEQUENCE DESCRIPTION: SEQ ID NO:3:

```
ATGAAGAACA CCTCCTCCCT CTGCCTCCTG CTGCTCGTGG TCCTCTGCTC CCTGACCTGC     60

AACAGCGGCC AGGCC                                                     75
```

(2) INFORMATION FOR SEQ ID NO:4:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (vii) IMMEDIATE SOURCE:
        (B) CLONE: codon-optimized RAmy3D signal-prosubtilisin BPN'

(xi) SEQUENCE DESCRIPTION: SEQ ID NO:4:

```
ATGAAGAACA CCTCCTCCCT CTGCCTCCTG CTGCTCGTGG TCCTCTGCTC CCTGACCTGC      60

AACAGCGGCC AGGCCGCTGG CAAGAGCAAC GGGGAGAAGA AGTACATCGT CGGCTTCAAG     120

CAGACCATGA GCACCATGAG CGCCGCCAAG AAGAAGGACG TCATCAGCGA AGGGCGGC       180

AAGGTACAGA AGCAGTTCAA GTACGTGGAC GCCGCCAGCG CCACCCTCAA CGAGAAGGCC     240

GTCAAGGAGC TGAAGAAGGA CCCGAGCGTC GCCTACGTCG AGGAGGACCA CGTCGCCCAC     300

GCATATGCAC AGAGCGTCCC GTACGGCGTC AGCCAGATCA AGGCCCCGGC CCTCCACAGC     360

CAGGGCTACA CCGGCAGCAA CGTCAAGGTC GCCGTCATCG ACAGCGGCAT CGACAGCAGC     420

CACCCGGACC TCAAGGTCGC CGGCGGAGCT AGCATGGTCC CGAGCGAGAC CAACCCGTTC     480

CAGGACACCA ACAGCCATGG CACCCACGTC GCCGGCACCG TCGCCGCCCT CAACAACAGC     540

ATCGGCGTCC TCGGCGTCGC CCCGAGCGCC AGCCTCTACG CCGTCAAGGT ACTCGGCGCC     600

GACGGCAGCG GCCAGTACAG CTGGATCATC AACGGCATCG AGTGGGCCAT CGCCAACAAC     660

ATGGACGTCA TCACCATGAG CCTCGGCGGC CCGAGCGGCA GCGCCGCCCT CAAGGCCGCC     720

GTCGACAAGG CCGTCGCCAG CGGCGTCGTC GTCGTCGCCG CCGCCGGCAA CGAGGGCACC     780

AGCGGCAGCA GCAGCACCGT CGGCTACCCG GGCAAGTACC CGAGCGTCAT CGCCGTCGGC     840

GCCGTGGACA GCAGCAACCA GCGCGCGAGC TTCAGCAGCG TCGGCCCGGA GCTGGACGTC     900

ATGGCCCCGG GCGTCAGCAT CCAGAGCACC CTCCCGGGCA ACAAGTACGG CGCCTACAGC     960

GGCACCAGCA TGGCCAGCCC GCACGTCGCC GGCGCCGCTG CACTCATCCT CAGCAAGCAC    1020

CCGACCTGGA CCAACACCCA GGTCCGCAGC AGCCTGGAGA ACACCACCAC CAAGCTCGGC    1080

GACAGCTTCT ACTACGGCAA GGGCCTCATC AACGTCCAGG CCGCCGCCCA GTGACTCGAG    1140
```

(2) INFORMATION FOR SEQ ID NO:5:

(i) SEQUENCE CHARACTERISTICS:
        (A) LENGTH: 1260 base pairs
        (B) TYPE: nucleic acid
        (C) STRANDEDNESS: single
        (D) TOPOLOGY: linear (vii) IMMEDIATE SOURCE:
        (B) CLONE: codon-optimized RAmy3D signal-mature AAT (xi) SEQUENCE DESCRIPTION: SEQ ID NO:5:

```
ATGAAGAACA CCTCCTCCCT CTGCCTCCTG CTGCTCGTGG TCCTCTGCTC CCTGACCTGC      60

AACAGCGGCC AGGCCGAGGA CCCGCAGGGC GACGCCGCCC AGAAGACCGA CACCAGCCAC     120

CACGACCAGG ACCACCCGAC GTTCAACAAG ATCACCCCGA ATTTGGCCGA ATTCGCCTTC     180

AGCCTGTACC GCCAGCTCGC GCACCAGTCC AACTCCACCA ACATCTTCTT CAGCCCGGTG     240

AGCATCGCCA CCGCCTTCGC CATGCTGTCC CTGGGTACCA AGGCGGACAC CCACGACGAG     300

ATCCTCGAAG GGCTGAACTT CAACCTGACG GAGATCCCGG AGGCGCAGAT CCACGAGGGC     360

TTCCAGGAGC TGCTCAGGAC GCTCAACCAG CCGGACTCCC AGCTCCAGCT CACCACCGGC     420
```

```
AACGGGCTCT TCCTGTCCGA GGGCCTCAAG CTCGTCGATA AGTTCCTGGA GGACGTGAAG       480

AAGCTCTACC ACTCCGAGGC GTTCACCGTC AACTTCGGGG ACACCGAGGA GGCCAAGAAG       540

CAGATCAACG ACTACGTCGA GAAGGGGACC CAGGGCAAGA TCGTGGACCT GGTCAAGGAA       600

TTGGACAGGG ACACCGTCTT CGCGCTCGTC AACTACATCT TCTTCAAGGG CAAGTGGGAG       660

CGCCCGTTCG AGGTGAAGGA CACCGAGGAG GAGGACTTCC ACGTCGACCA GGTCACCACC       720

GTCAAGGTCC CGATGATGAA GAGGCTCGGC ATGTTCAACA TCCAGCACTG CAAGAAGCTC       780

TCCAGCTGGG TGCTCCTCAT GAAGTACCTG GGGAACGCCA CCGCCATCTT CTTCCTGCCG       840

GACGAGGGCA AGCTCCAGCA CCTGGAGAAC GAGCTGACGC ACGACATCAT CACGAAGTTC       900

CTGGAGAACG AGGACAGGCG CTCCGCTAGC CTCCACCTCC CGAAGCTGAG CATCACCGGC       960

ACGTACGACC TGAAGAGCGT GCTGGGCCAG CTGGGCATCA CGAAGGTCTT CAGCAACGGC      1020

GCGGACCTCT CCGGCGTGAC GGAGGAGGCC CCCCTGAAGC TCTCCAAGGC CGTGCACAAG      1080

GCGGTGCTCA CGATCGACGA GAAGGGGACG GAAGCTGCCG GGGCCATGTT CCTGGAGGCC      1140

ATCCCCATGT CCATCCCGCC CGAGGTCAAG TTCAACAAGC CCTTCGTCTT CCTGATGATC      1200

GAGCAGAACA CGAAGAGCCC CCTCTTCATG GGGAAGGTCG TCAACCCCAC GCAGAAGTGA      1260

(2) INFORMATION FOR SEQ ID NO:6:

(i) SEQUENCE CHARACTERISTICS:
        (A) LENGTH: 1382 base pairs
        (B) TYPE: nucleic acid
        (C) STRANDEDNESS: single
        (D) TOPOLOGY: linear (vii) IMMEDIATE SOURCE:
        (B) CLONE: codon opt RAmy3D-native mature ATIII (xi) SEQUENCE DESCRIPTION: SEQ ID NO:6:

ATGAAGAACA CCTCCTCCCT CTGCCTCCTG CTGCTCGTGG TCCTCTGCTC CCTGACCTGC        60

AACAGCGGCC AGGCCCACGG AAGCCCTGTG ACATCTGCA CAGCCAAGCC GCGGGACATT       120

CCCATGAATC CCATGTGCAT TTACCGCTCC CCGGAGAAGA AGGCAACTGA GGATGAGGGC       180

TCAGAACAGA AGATCCCGGA GGCCACCAAC CGGCGTGTCT GGGAACTGTC CAAGGCCAAT       240

TCCCGCTTTG CTACCACTTT CTATCAGCAC CTGGCAGATT CCAAGAATGA CAATGATAAC       300

ATTTTCCTGT CACCCCTGAG TATCTCCACG GCTTTTGCTA TGACCAAGCT GGGTGCCTGT       360

AATGACACCC TCCAGCAACT GATGGAGGTA TTTAAGTTTG ACACCATATC TGAGAAAACA       420

TCTGATCAGA TCCACTTCTT CTTTGCCAAA CTGAACTGCC GACTCTATCG AAAAGCCAAC       480

AAATCCTCCA AGTTAGTATC AGCCAATCGC CTTTTTGGAG ACAAATCCCT TACCTTCAAT       540

GAGACCTACC AGGACATCAG TGAGTTGGTA TATGGAGCCA AGCTCCAGCC CCTGGACTTC       600

AAGGAAAATG CAGAGCAATC CAGAGCGGCC ATCAACAAAT GGGTGTCCAA TAAGACCGAA       660

GGCCGAATCA CCGATGTCAT TCCCTCGGAA GCCATCAATG AGCTCACTGT TCTGGTGCTG       720

GTTAACACCA TTTACTTCAA GGGCCTGTGG AAGTCAAAGT TCAGCCCTGA GAACACAAGG       780

AAGGAACTGT TCTACAAGGC TGATGGAGAG TCGTGTTCAG CATCTATGAT GTACCAGGAA       840

GGCAAGTTCC GTTATCGGCG CGTGGCTGAA GGCACCCAGG TGCTTGAGTT GCCCTTCAAA       900

GGTGATGACA TCACCATGGT CCTCATCTTG CCCAAGCCTG AGAAGAGCCT GGCCAAGGTG       960

GAGAAGGAAC TCACCCCAGA GGTGCTGCAG GAGTGGCTGG ATGAATTGGA GGAGATGATG      1020

CTGGTGGTTC ACATGCCCCG CTTCCGCATT GAGGACGGCT TCAGTTTGAA GGAGCAGCTG      1080
```

-continued

```
CAAGACATGG GCCTTGTCGA TCTGTTCAGC CCTGAAAAGT CCAAACTCCC AGGTATTGTT      1140

GCAGAAGGCC GAGATGACCT CTATGTCTCA GATGCATTCC ATAAGGCATT TCTTGAGGTA      1200

AATGAAGAAG GCAGTGAAGC AGCTGCAAGT ACCGCTGTTG TGATTGCTGG CCGTTCGCTA      1260

AACCCCAACA GGGTGACTTT CAAGGCCAAC AGGCCCTTCC TGGTTTTTAT AAGAGAAGTT      1320

CCTCTGAACA CTATTATCTT CATGGGCAGA GTAGCCAACC CTTGTGTTAA GTAACTCGAG      1380

CC                                                                    1382
```

(2) INFORMATION FOR SEQ ID NO:7:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (vii) IMMEDIATE SOURCE:
        (B) CLONE: RAmy1A 5' untranslated region (5' UTR)

(xi) SEQUENCE DESCRIPTION: SEQ ID NO:7:

```
ATCAATCATC CATCTCCGAA GTGTGTCTGC AGCATGCAGG TGCTGAACAC C                51
```

(2) INFORMATION FOR SEQ ID NO:8:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (vii) IMMEDIATE SOURCE:
        (B) CLONE: RAmy1A 3' untranslated region (3' UTR)

(xi) SEQUENCE DESCRIPTION: SEQ ID NO:8:

```
GCGCACGATG ACGAGACTCT CAGTTTAGCA GATTTAACCT GCGATTTTTA CCCTGACCGG        60

TATACGTATA TACGTGCCGG CAACGAGCTG TATCCGATCC GAATTACGGA TGCAATTGTC       120

CACGAAGTAC TTCCTCCGTA AATAAAGTAG GATCAGGGAC ATACATTTGT ATGGTTTTAC       180

GAATAATGCT ATGCAATAAA ATTTGCACTG CTTAATGCTT ATGCATTTTT GCTTGGTTCG       240

ATTGTACTGG TGAATTATTG TTACTGTTCT TTTTACTTCT CGAGTGGCAG TATTGTTCTT       300

CTACGAAAAT TTGATGCGTA G                                                 321
```

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: N-terminal amino acid sequence of mature AAT (xi) SEQUENCE DESCRIPTION: SEQ ID NO:9:

```
Glu Asp Pro Gln Gly Asp Ala Ala Gln Lys Thr Asp Thr
 1               5                  10
```

(2) INFORMATION FOR SEQ ID NO:10:

(i) SEQUENCE CHARACTERISTICS:
        (A) LENGTH: 1308 base pairs
        (B) TYPE: nucleic acid (C) STRANDEDNESS: single
            (D) TOPOLOGY: linear (xi) SEQUENCE DESCRIPTION: SEQ ID NO:10:

GCGGCCGCTC ACTATCGAAC ACGGTTTCAG CTTACACAGA TATGAAGAAC ACCTCCTCCC        60

TCTGCCTCCT GCTGCTCGTG GTCCTCTGCT CCCTGACCTG CAACAGCGGC CAGGCGGAGG       120

ACCCGCAGGG CGACGCCGCC CAGAAGACCG ACACCAGCCA CCACGACCAG GACCACCCGA       180

CGTTCAACAA GATCACCCCG AATTTGGCCG AATTCGCCTT CAGCCTGTAC CGCCAGCTCG       240

CGCACCAGTC CAACTCCACC AACATCTTCT TCAGCCCGGT GAGCATCGCC ACCGCCTTCG       300

CCATGCTGTC CCTGGGTACC AAGGCGGACA CCCACGACGA GATCCTCGAA GGGCTGAACT       360

TCAACCTGAC GGAGATCCCG GAGGCGCAGA TCCACGAGGG CTTCCAGGAG CTGCTCAGGA       420

CGCTCAACCA GCCGGACTCC CAGCTCCAGC TCACCACCGG CAACGGGCTC TTCCTGTCCG       480

AGGGCCTCAA GCTCGTCGAT AAGTTCCTGG AGGACGTGAA GAAGCTCTAC CACTCCGAGG       540

CGTTCACCGT CAACTTCGGG GACACCGAGG AGGCCAAGAA GCAGATCAAC GACTACGTCG       600

AGAAGGGGAC CCAGGGCAAG ATCGTGGACC TGGTCAAGGA ATTGGACAGG GACACCGTCT       660

TCGCGCTCGT CAACTACATC TTCTTCAAGG GCAAGTGGGA GCGCCCGTTC GAGGTGAAGG       720

ACACCGAGGA GGAGGACTTC CACGTCGACC AGGTCACCAC CGTCAAGGTC CCGATGATGA       780

AGAGGCTCGG CATGTTCAAC ATCCAGCACT GCAAGAAGCT CTCCAGCTGG GTGCTCCTCA       840

TGAAGTACCT GGGGAACGCC ACCGCCATCT TCTTCCTGCC GGACGAGGGC AAGCTCCAGC       900

ACCTGGAGAA CGAGCTGACG CACGACATCA TCACGAAGTT CCTGGAGAAC GAGGACAGGC       960

GCTCCGCTAG CCTCCACCTC CCGAAGCTGA GCATCACCGG CACGTACGAC CTGAAGAGCG      1020

TGCTGGGCCA GCTGGGCATC ACGAAGGTCT TCAGCAACGG CGCGGACCTC TCCGGCGTGA      1080

CGGAGGAGGC CCCCCTGAAG CTCTCCAAGG CCGTGCACAA GGCGGTGCTC ACGATCGACG      1140

AGAAGGGGAC GGAAGCTGCC GGGGCCATGT TCCTGGAGGC CATCCCCATG TCCATCCCGC      1200

CCGAGGTCAA GTTCAACAAG CCCTTCGTCT TCCTGATGAT CGAGCAGAAC ACGAAGAGCC      1260

CCCTCTTCAT GGGGAAGGTC GTCAACCCCA CGCAGAAGTG AGCTCGAG                   1308

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:11:

GCTTGACCTG TAACTCGGGC CAGGCGAGCT                                         30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:12:

CGCCTAGCCC GAGTTACAGG TCAAGCAGCT                                         30

(2) INFORMATION FOR SEQ ID NO:13:

(i) SEQUENCE CHARACTERISTICS:

```
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:13:

AGCTCCATGG CCGTGGCTCG AGTCTAGACG CGTCCCC                    37

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:14:

GGGGACGCGT CTAGACTCGA GCCACGGCCA TGG                        33

(2) INFORMATION FOR SEQ ID NO:15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:15:

GCATGCAGGT GCTGAACACC ATGGTGAACA AACAC                      35

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:16:

TTCTTGTCCC TTTCGGTCCT CATCGTCCTC CT                         32

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:17:

TGGCCTCTCC TCCAACTTGA CAGCCGGGAG CT                         32

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:18:

TTCACCATGG TGTTCAGCAC CTGCATGCTG CA                         32

(2) INFORMATION FOR SEQ ID NO:19:

(i) SEQUENCE CHARACTERISTICS:
        (A) LENGTH: 32 base pairs
```

(B) TYPE: nucleic acid
            (C) STRANDEDNESS: single
            (D) TOPOLOGY: linear (xi) SEQUENCE DESCRIPTION: SEQ ID NO:19:

CGATGAGGAC CGAAAGGGAC AAGAAGTGTT TG                32

(2) INFORMATION FOR SEQ ID NO:20:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:20:

CCCGGCTGTC AAGTTGGAGG AGAGGCCAAG GAGGA             35

(2) INFORMATION FOR SEQ ID NO:21:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:21:

CCGTGTTCGA TAGTGAGCGG CCGCTAACCA CTACTGATC         39

(2) INFORMATION FOR SEQ ID NO:22:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:22:

GTTTCAGCTT ACACAGATGC GGCCGCCACC AGCAGCTTGT GT     42

(2) INFORMATION FOR SEQ ID NO:23:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:23:

CCTTTCAACA TGTTGTAGCG GCCGCCCTGC TGCTTCCACG        40